United States Patent [19]

Kneuper et al.

[11] Patent Number: 5,895,816
[45] Date of Patent: Apr. 20, 1999

[54] PREPARATION OF ALKYLAMINES

[75] Inventors: Heinz-Josef Kneuper; Rolf Lebkücher, both of Mannheim; Horst Neuhauser, Dudenhofen; Andreas Henne, Neustadt; Rainer Becker, Bad Dürkheim, all of Germany

[73] Assignee: BASF Aktiengesellschaft, Ludwigshafen, Germany

[21] Appl. No.: 09/115,799

[22] Filed: Jul. 15, 1998

[30] Foreign Application Priority Data

Jul. 23, 1997 [DE] Germany .................... 197 31 745

[51] Int. Cl.$^6$ .................................................. C07D 295/03

[52] U.S. Cl. .................... 544/404; 544/471; 544/473

[58] Field of Search ......................... 544/404, 471, 544/473

[56] References Cited

U.S. PATENT DOCUMENTS

| 3,249,613 | 5/1966 | Burns et al. | 260/268 |
| 3,948,900 | 4/1976 | Moss | 260/268 |
| 4,952,734 | 8/1990 | Weber et al. | 564/471 |
| 5,414,087 | 5/1995 | Speranza et al. | 544/404 |

OTHER PUBLICATIONS

Forsee et al., *J. Am. Chem. Soc.*, vol. 57, pp. 2363–2364, Dec. 1935.

*Primary Examiner*—Brian M. Burn
*Attorney, Agent, or Firm*—Keil & Weinkauf

[57] ABSTRACT

In a process for preparing alkylamines by reacting amines and aliphatic aldehydes in the presence of free hydrogen on a fixed bed catalyst in a reactor in which amines and aldehydes are mixed in the catalyst bed after being fed in in separate streams, only the aldehyde stream or only the amine stream is preheated during the feeding in.

10 Claims, No Drawings

PREPARATION OF ALKYLAMINES

The invention relates to a process for preparing alkylamines.

The preparation of alkylamines by reacting amines with aldehydes to give alkanolamines, which are subsequently hydrogenated to alkylamines, is known. U.S. Pat. No. 3,249,613, for example, describes the reaction of piperazine with formaldehyde to give 1,4-piperazinedimethanol, which is subsequently hydrogenated to 1,4-dimethylpiperazine using a metallic hydrogenation catalyst. Corresponding reactions are described in DE-A-25 31 060.

It is advantageous to carry out the process for preparing alkylamines continuously. However, mixing of the amines and aldehydes used results in the formation of polymeric condensation products which are insoluble in all ordinary solvents, see W. T. Forsee, Jr. C. B. Pollard, J. Am. Chem. Soc. 57, 1935, 2363–2364. Reaction and hydrogenation of the polymeric condensation product is impossible. Attempts have therefore been made to avoid this problem by special procedures.

A process for the continuous preparation of methylamines from amines, formaldehyde and hydrogen is also known. EP-A-0 297 295 describes such a process in which amines, formaldehyde and hydrogen are converted into methylamines in one step in the liquid phase in a fixed bed catalyst at elevated temperature under pressure. This process is used in particular to prepare N,N-dimethyl-n-octylamine, N,N-dimethylaniline, N,N-dimethylpiperazine and N,N-dimethyldiglycolamine.

In order to prevent decomposition of the catalyst, EP-A 0 297 295 discloses limiting the water content of the mixture present in the reactor. The total of the water contents of the feed streams should not exceed 50% by weight. In particular, the water content of the formaldehyde solution should be from 7 to 15% by weight. In addition, it emerges that it is crucial to heat the amine stream and form aldehyde stream separately to a preset temperature by passing them and heating them through their own lines before the reaction is carried out.

The disadvantages of the process are the high cost of the apparatus for the separate preheating of the reactants and the need to use a concentrated formaldehyde solution. Formaldehyde is normally sold as an approximately 30% by weight solution in water. Increasing the formaldehyde concentration before the reaction increases the elaboration and makes the process very costly.

It is an object of the present invention to provide a process for preparing alkylamines which avoids the above disadvantages and, in particular, can be carried out economically in a simplified industrial setup. It is intended that commercial products be useable as starting materials.

We have found that this object is achieved by a process for preparing alkylamines by reacting amines and aliphatic aldehydes in the presence of free hydrogen on a fixed bed catalyst in a reactor in which amines and aldehydes are mixed in the catalyst bed after being fed in in separate streams, wherein only the aldehyde stream or only the amine stream is preheated during the feeding in.

It has been found according to the invention that alkylamines can be prepared continuously by reacting amines and aliphatic aldehydes in the presence of free hydrogen if only one of the streams of the reactants is preheated during the feeding in. The process can moreover be carried out using water-containing reactants, and the water content can be high. This does not damage the fixed bed catalyst employed.

It is possible to use in the process according to the invention for example commercial formaldehyde which is usually marketed as 30 to 40% by weight solution in water. An increase in the formaldehyde concentration which is necessary for known processes can be omitted. In addition, the apparatus used to prepare the alkylamines can be simplified by the need to preheat only one reactant stream. Since the process is usually carried out under high pressure, the heat exchangers employed for the preheating must be suitable for the high pressure conditions. Heat exchangers of this type are costly.

Amines employed according to the invention preferably have at least one secondary amino group. They are particularly preferably secondary amines having 1 to 3 amino groups. Examples of suitable amines are diethylenetriamine, dipropylenetriamine, morpholine, piperidine, pyrrolidine, piperazine, 1-methylpiperazine, and piperazine is employed in particular in the process according to the invention. The amines can be employed without added solvents or in the form of solutions. Alcohols are preferably not employed as solvents. Alcohols may be formed in small amounts from the aldehydes employed where appropriate. It is preferable for no alcohols at all to be present in the reaction system. The amines are particularly preferably employed as aqueous solutions. For example, piperazine is employed as 30 to 80% by weight solution in water. The piperazine concentration is, in particular, about 60 to 70% by weight.

The aliphatic aldehydes employed according to the invention may have one or more aldehyde functionalities. They are preferably mono- or dialdehydes, in particular monoaldehydes. The aldehydes moreover preferably have from 1 to 10, preferably 1 to 3, in particular 1 or 2, carbon atoms. Formaldehyde is especially preferably employed.

The aldehydes are likewise preferably employed as aqueous solutions. In this case, the water content of the aldehyde solution is from 50 to 90, preferably from 50 to 80, in particular from 60 to 80, specifically from 65 to 75, % of the total weight of the solution.

Reaction of the amines with the aliphatic aldehydes results in alkyl substitution on the nitrogen atom, and the introduced alkyl radical has a number of carbon atoms corresponding to the number of carbon atoms in the aldehyde. Thus, a methylation is carried out on use of formaldehyde. The secondary amines which are preferably employed are preferably peralkylated or permethylated. Thus, piperazine, which is especially preferred, is converted into 1,4-dimethylpiperazine. It was moreover intended that the content of monoalkylated compounds, specifically N-methylpiperazine, be minimized.

The reactant streams fed into the reactor may have a high water content without the reactor or catalyst being damaged. For example, the total of the water contents of the streams of the amine and aldehyde solutions fed into the reactor can be from 50 to 80, preferably from 50 to 70, in particular from 55 to 70, specifically from 60 to 70, % of the total weight of the streams.

The molar ratio of the preferred reactants piperazine and formaldehyde is preferably from 1:1.0 to 1:5, particularly preferably 1:1.5 to 1:3, in particular 1:2 to 1:2.7.

The reaction is carried out on a fixed bed catalyst. All suitable fixed bed catalysts can be employed for this purpose. The fixed bed catalyst is preferably an unsupported catalyst which, in the oxide form, contains at least 60% by weight of CoO and from 10 to 30% by weight of CuO, based on the total weight of the catalyst, it being possible for up to one third of the amount of CoO to be replaced by NiO.

The catalyst can moreover contain small amounts of other substances, for example chromium, aluminum, silver, alkali metals and/or alkaline earth metals or their compounds, vanadium, tungsten, boron or their compounds, noble metals of the platinum series, phosphoric acid and, particularly preferably, manganese and molybdenum or their compounds. The catalyst may additionally contain small amounts of substances usually employed as carriers without loosing the characteristics of an unsupported catalyst. A particularly preferred catalyst contains, in the oxide form, CoO, CuO, $Mn_3O_4$ and $MoO_3$. In particular, it consists essentially (more than 90% by weight) or completely of these constituents. An especially preferred catalyst has the following rough composition: 60–70% CoO, 15–25% CuO, 5–10% $Mn_3O_4$ and 0–0% $MoO_3$. The percentages are % by weight in each case.

Catalysts of this type are described, for example, in DE-A 26 18 580. Processes for preparing the catalysts are also described in this publication.

The process according to the invention is preferably carried out at from 60 to 200° C., particularly preferably 80 to 160° C. In these cases, the total pressure is preferably from 10 to 700, particularly preferably 100 to 300 bar.

The reactor used for this purpose is preferably a tubular reactor which can be operated, for example, by an upflow or downflow method. In the process according to the invention, the aqueous piperazine solution is preferably heated by a heat exchanger to about 100° C. and passed at this temperature into the tubular reactor. The aqueous formaldehyde solution is likewise passed, without previous heating, into the tubular reactor, with the feed terminating in the catalyst bed. This ensures that mixing of the reactants takes place only in the catalyst bed. It is also possible for the reactor to have a different design as long as it is ensured that there is negligible mixing of the amines and aldehydes before contacting the catalyst.

It is possible with the process according to the invention to achieve conversions of more than 99.9% and selectivities of more than 99.8%, with the residue comprising less than 0.5% by weight.

The invention is explained in detail by means of examples hereinafter.

Comparative Example C1

A 60% by weight solution of piperazine in water and a 30% by weight solution of formaldehyde in water were mixed at room temperature. The white solid which formed was not soluble in any conventional solvent.

EXAMPLE 1

A tubular reactor was equipped with 2 separate inflow lines so that it could be operated by a downflow method. The inflow line for formaldehyde extended as far as the catalyst bed. The piperazine/water inflow was preheated to about 100° C. before reaching the catalyst bed. The catalyst employed had the following rough composition (in % by weight): 65% CoO, 20% CuO, 10% $Mn_3O_4$, 5% $MoO_3$. The reaction was carried out at 100° C. under a pressure of 200 bar of hydrogen. The space velocity was 0.12 1/l h based on piperazine. The molar ratio of piperazine to formaldehyde was 1:2.3. The tubular reactor could be operated for more than 12 days without a blockage occurring. The conversion and selectivity were in each case more than 99.8%, with less than 0.5% by weight of residue being obtained. There was no detectable damage to or deactivation of the catalyst.

EXAMPLE 2

Example 1 was repeated but the formaldehyde feed was divided at the top of the reactor, and the two inflows were passed onto the catalyst bed on opposite sides of the reactor wall. The reactor could be operated for more than 4 days with the same result as indicated in Example 1.

We claim:

1. A process for preparing alkylamines by reacting amines and aliphatic aldehydes in the presence of free hydrogen on a fixed bed catalyst in a reactor in which amines and aldehydes are mixed in the catalyst bed after being fed in in separate streams, wherein only the aldehyde stream or only the amine stream is preheated during the feeding in.

2. A process as claimed in claim 1 wherein the amine stream, but not the aldehyde stream, is preheated.

3. A process as claimed in claim 1, wherein amines and/or aldehydes are employed as aqueous solutions.

4. A process as claimed in claim 3, wherein the aqueous solution of the aldehyde contains from 50 to 90% by weight of water based on the total weight of the solution.

5. A process as claimed in claim 3, wherein the total of the water contents of the streams of the amine and aldehyde solutions fed into the reactor is from 50 to 80% of the total weight of the streams.

6. A process as claimed in claim 1, wherein the fixed bed catalyst is an unsupported catalyst which, in the oxide form, contains at least 60% by weight of CoO and from 10 to 30% by weight of CuO, based on the total weight of the catalyst, it being possible for up to one third of the amount of CoO to be replaced by NiO.

7. A process as claimed in claim 1, wherein the amine is a secondary amine having 1 to 3 amino groups.

8. A process as claimed in claim 7, wherein the amine is piperazine.

9. A process as claimed in claim 1, wherein the aldehyde is formaldehyde.

10. A process as claimed in claim 1, wherein the reaction results in peralkylated amines.

* * * * *